United States Patent [19]

Junien et al.

[11] Patent Number: 5,326,784
[45] Date of Patent: Jul. 5, 1994

[54] CYCLOALKYLALKYLAMINES WHICH ARE SIGMA-RECEPTOR LIGANDS AND THEIR APPLICATION IN THERAPY

[75] Inventors: Jean-Louis Junien, Sevres; Alain Calvet, L'Hay-les-Roses; Henri Jacobelli, Paray-Vieille-Poste; Francois Roman, Vitry-sur-Seine, all of France

[73] Assignee: Institut de Recherche Jouveinal, Fresnes, France

[21] Appl. No.: 99,299

[22] Filed: Jul. 29, 1993

[30] Foreign Application Priority Data

Jul. 31, 1992 [FR] France .................. 92 09536

[51] Int. Cl.⁵ .......... A61K 31/135; A61K 31/35; C07C 211/19; C07D 311/74
[52] U.S. Cl. .................. 514/456; 514/462; 514/528; 514/640; 514/657; 549/331; 549/336; 549/401; 549/404; 558/415; 558/418; 564/265; 564/378
[58] Field of Search .............. 549/331, 336, 401, 404; 558/415, 418; 564/265, 378; 514/456, 462, 528, 640, 657

[56] References Cited

U.S. PATENT DOCUMENTS 5,180,746  1/1993  Goto et al. .................. 564/373

OTHER PUBLICATIONS

Welch et al, J. Med. Chem. (1977), vol. 20, No. 5, pp. 699–705.
Krotov et al, Chemical Abstracts, vol. 52 (1958) 20677b.

*Primary Examiner*—Richard L. Raymond
*Attorney, Agent, or Firm*—Pennie & Edmonds

[57] ABSTRACT

New cycloalkylalkylamines which are sigma-receptor ligands of formule (I)

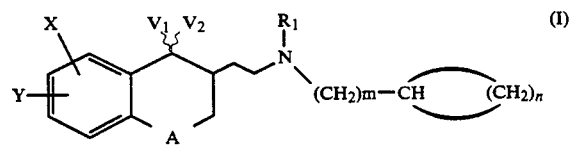

in which: $R_1$ is H or lower alkyl; X and Y are H, OH, lower alkyl, lower alkoxy, halogen or nitrile; $V_1$ and $V_2$ together form a double bond attached to an oxygen atom or to a hydroxyimino radical, or are linked as an ethylenedioxy chain; A represents a valency bond, an oxygen atom, a methylene or an ethylene group; m is equal to 0, 1 or 2; n has the value of an integer from 1 to 5. Psychotropic drug which is also useful in gastroenterology.

18 Claims, No Drawings

CYCLOALKYLALKYLAMINES WHICH ARE SIGMA-RECEPTOR LIGANDS AND THEIR APPLICATION IN THERAPY

The present invention relates to new cycloalkylalkylamines which are sigma-receptor ligands, to a process for preparing them and to their application in therapy.

From the time the sigma receptors were first detected, the large amount of work performed in relation to them has shown their involvement in various mental dysfunctions and, more recently, their local involvement in certain gastrointestinal disorders. Consequently, for several years, numerous molecules of various chemical structures aimed at possessing an affinity for sigma receptors, and for which their use has been envisaged in the treatment of psychoses and/or of gastrointestinal disorders, have been proposed.

In fact, most of these compounds are not specific ligands for sigma receptors, and interact with other receptors including the phencyclidine (PCP) receptors and the dopaminergic ($D_2$) receptors; as a result of this multiplicity of affinities, they cannot be used for the therapeutic applications envisaged without the risk of giving rise to serious side effects, such as extrapyramidal manifestations which can be reversed only with difficulty or only partially.

The best known of these molecules belong to chemically disparate families and are, inter alia:

N-allylnormetazocine (SKF 10047) and cyclazocine, which have a benzomorphan type structure and which, apart from their sigma affinity, have a strong affinity for phencyclidine (PCP) receptors, the latter being involved in psychotic manifestations reflected in disorientation, excitation or hallucination states;

1,3-di-o-tolylguanidine (DTG), the characteristic chemical sequence of which is a guanidine and which, apart from its difficulty in crossing the blood-brain barrier, causes symptoms in rats similar to those of PCP;

(+)-3-(3-hydroxyphenyl)-N-(1-propyl)piperidine (+)-3-PPP, which shows a strong affinity for dopaminergic ($D_2$) receptors;

haloperidol (INN), which is 4-[4-(p-chlorophenyl)-4-hydroxypiperidino]-4'-fluorobutyrophenone, used for its neuroleptic properties and which is also regarded as a reference sigma ligand compound, although its use proves to be particularly exacting on account of its strong affinity for dopaminergic $D_2$ receptors, which can induce extrapyramidal disorders of the cataleptic type.

Overcoming the difficulties of the state of the art, new compounds have just been discovered which possess exceptional affinity for sigma receptors while being substantially devoid of these undesirable affinities referred to above. This sigma activity is expressed in concrete form "in vivo" in animals by the capacity of the compounds to inhibit convulsions caused by electric shock and also to inhibit cysteamine-induced ulcers, thereby sanctioning their use as therapy for certain disorders of the central nervous system and/or of the gastrointesinal tract.

The present invention hence relates to new compounds which are cycloalkylalkylamines and which are sigma-receptor ligands and of general formula (I)

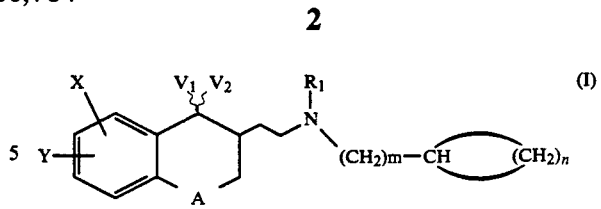

in which:

$R_1$ is H or lower alkyl;

X and Y, which may be identical or different, are H, OH, lower alkyl, lower alkoxy, halogen or nitrile;

$V_1$ and $V_2$ together form a double bond attached to an oxygen atom or else to a hydroxyimino radical N—OH, or else are linked as an ethylenedioxy chain —O—$CH_2$—$CH_2$—O;

A represents a valency bond, an oxygen atom, a methylene group or alternatively an ethylene group.

m is equal to 0, 1 or 2;

n has the value of an integer from 1 to 5.

The invention relates both to the racemic or optically active forms of these compounds (I) and to their addition salts with pharmaceutically acceptable acids. To this end, as an example, the salts with acetic, benzenesulfonic, camphorsulfonic, citric, ethanesulfonic, fumaric, hydrobromic, lactic, maleic, malic, methanesulfonic, mucic, nitric, pamoic, phosphoric, salicylic, stearic, succinic, sulfuric and tartaric acids and, more especially, hydrochloric acid are used.

Among the above-mentioned parameters, lower alkyl and lower alkoxy are substituents of 1–4 carbon atoms halogen means chlorine, or bromine, or more especially fluorine.

From among this set of compounds, those are preferred in which $V_1$ and $V_2$ together form a double bond attached to an oxygen atom, A is equal to $CH_2$ thus forming a ring containing 6 carbon atoms, and $R_1$ is lower alkyl, and which are embraced by the formula (I.a)

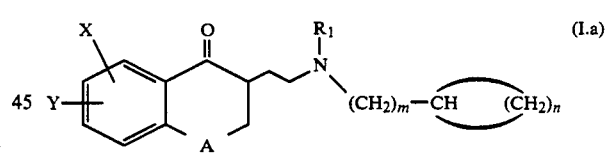

The compounds (I.a) in which $R_1$ is $CH_3$, m=1 or 2 and n=2 or 3 are especially preferred.

As indicated, the pharmacological studies of the compounds of the invention show a surprising sigma affinity which could not be foreseen in the light of the teaching of the prior art.

U.S. Pat. No. 3,189,612 includes a description of structures derived from indanone, synthesis intermediates for the preparation of the compounds to which the invention relates, antihistaminic compounds of formula (A)

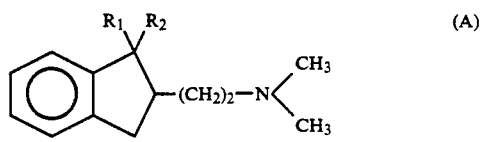

in which $R_1$ and $R_2$ are essentially lower alkyl groups. No mention is made of any pharmacological activity for the indanone compounds in which $R_1$ and $R_2$ together form a ketone function.

U.S. Pat. No. 4,564,641 includes a description of tetrahydronaphthalene derivatives of formula (B)

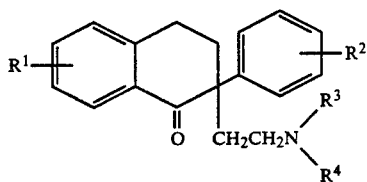
(B)

in which: $R_1$ and $R_2$ are identical or different and are each hydrogen, halogen, trifluoromethyl, $C_1$-$C_4$-alkyl or $C_1$-$C_4$-alkoxy, $R_3$ is $C_1$-$C_6$-alkyl and $R_4$ is hydrogen, $C_1$-$C_6$-alkyl or benzyl, or alternatively $R_3$ and $R_4$ together can form a $C_2$-$C_5$-alkyl chain. The compounds described in this patent are different from those of the present invention, in particular in respect of their chemical structure, which is characterized in that the carbon adjacent to the carbonyl function is substituted both with a phenyl radical and with an N-mono- or N-disubstituted aminoethyl radical; moreover, these compounds are stated to show inhibitory activity with respect to noradrenaline reuptake. In no case have the various pharmacological papers published subsequently to the patent indicated an affinity of these compounds for sigma receptors.

The paper published in J. Med. Chem., 1977, Vol. 20, No. 5, 699-705, includes, more especially, a description of compounds of general formula (C)

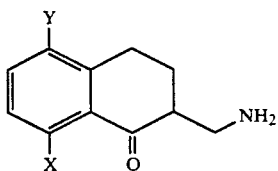
(C)

which possess analgesic and tranquillizing activity. Their chemical structure is different from that of the new compounds of the invention; thus, their carbon chain linking the tetralone ring-system to the nitrogen atom contains only a single carbon atom and, moreover, the nitrogen atom is in no case substituted with a cycloalkylalkyl radical of any kind.

European Patent Application No. 0,383,318 includes a description of aralkylamines of formula (D)

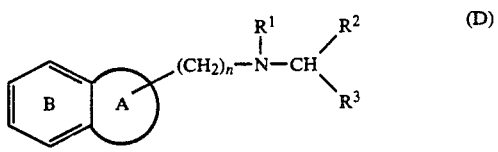
(D)

in which: $R_1$ is hydrogen or lower alkyl; $R_2$ is an aromatic group L which can be substituted; $R_3$ is hydrogen, a lower alkyl group or an aromatic group which can be substituted; n can assume values from 0 to 7; A is an optionally substituted ring of 5 to 8 carbon atoms which can comprise one or two hetero atoms which are oxygen and sulfur; and B is a benzene ring which can be substituted, and the physiologically acceptable salts of these compounds, which are used as cholinesterase inhibitors and as agents improving cerebral function.

The compounds of this European application are different from the new compounds according to the invention of formula (I) in respect of their chemical structure, in particular in respect of the nature of the substituents on the amine function which, in Application 0,383,318, expressly comprises an aromatic group $R_2$ which is absent from the structures of the present invention, and, moreover, in respect of the carbon chain linking the ring A to the amine function which can comprise from 0 to 7 carbon atoms whereas, in the present invention, this chain is exclusively composed of two carbon atoms.

Also, the compounds of Application 0,383,318 differ from the present invention in their cholinesterase-inhibitory property, while they are not described as being sigma-receptor ligands or active with respect to the gastrointestinal tract.

Another aspect of the present invention is directed towards a process for preparing the compounds of formula (I) and their salts. Essentially, the process for preparing a compound (I) of formula (I.a) in which X, Y, A, $R_1$, m and n have the meanings defined above consists, as shown in Scheme 1:

SCHEME 1

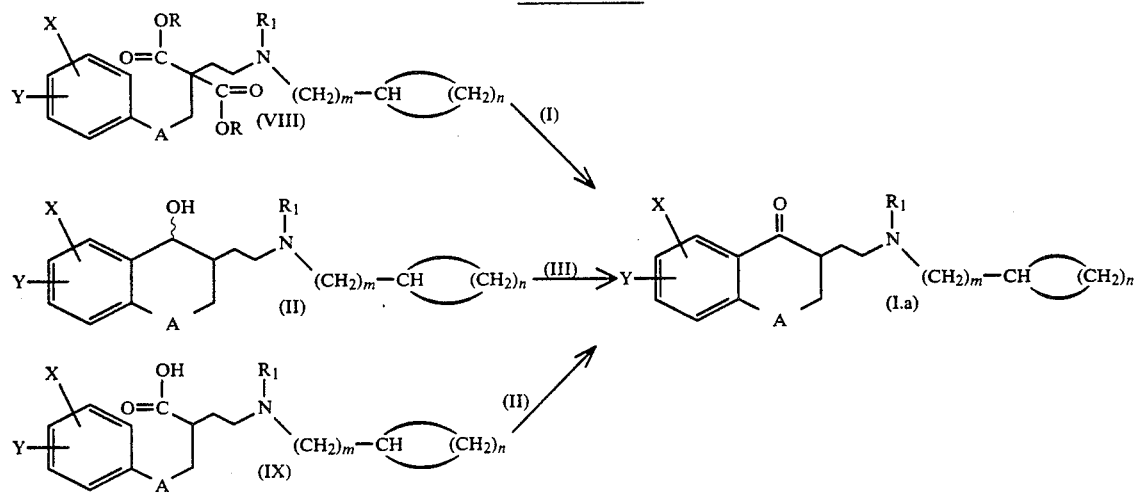

i) in cyclizing and decarboxylating by heating in an acid medium a malonic intermediate (VIII)

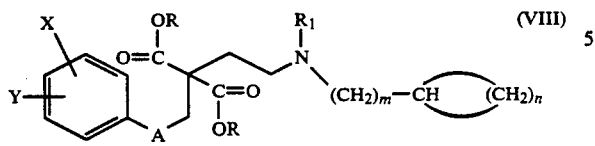

in which R is hydrogen, lower alkyl or a lower cycloalkyl, or ii) in cyclizing an acid intermediate (IX)

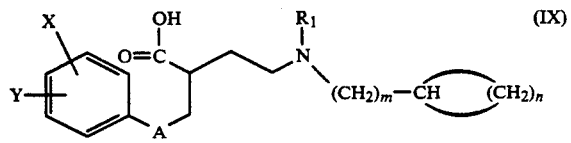

by a Friedel-Crafts type acylation method, or iii) according to the preferred process, in oxidizaing the hydroxyl function of an aminio alcohol (II)

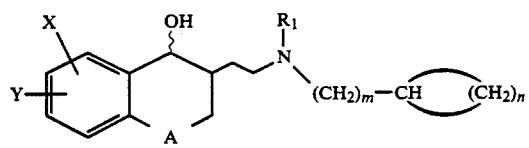

with a suitable oxidizing reagent, and, as shown in Scheme 2,

—O—$CH_2$—$CH_2$—O—, and which corresponds to the formula (I.c)

in reacting a compound (I.a) by condensation with ethylene glycol, optionally in the presence of a catalyst or, according to the preferred method, in reducing with a metal or organometallic hydride an intermediate amide (III.a) of formula

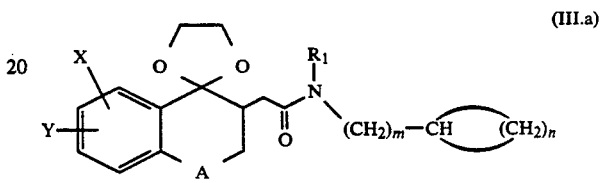

The preparation processes as set out make use of the intermediates (II), (III.a), (VIII) and (IX), the preparation of which is reported in the next part of this specification.

Generally speaking, the first process, as shown in Scheme 1, consists in cyclizing and then decarboxylating by heating in an acid medium a malonic intermediate (VIII) in order to obtain the compound (I.a). Such

SCHEME 2

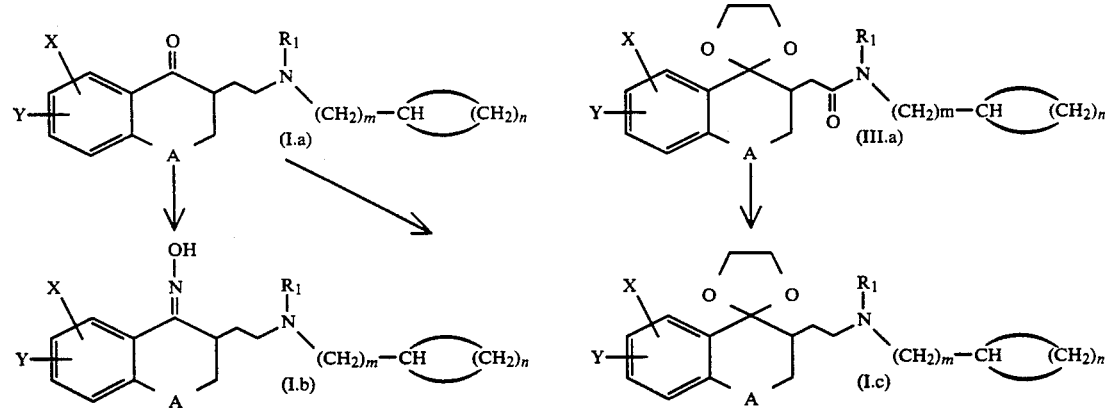

for preparing a compound of the invention (I) in which $V_1$ and $V_2$ form a double bond attached to a hydroxyimino radical =N—OH, and which corresponds to the formula (I.b)

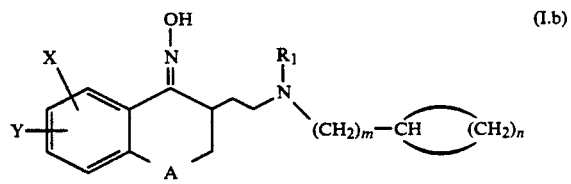

in reacting a compound (I.a) with hydroxylamine and, for preparing a compound of the invention (I) in which $V_1$ and $V_2$ are linked as an ethylenedioxy chain intermediates (VIII) used in this reaction are known, and may be prepared, in particular, according to the method described in U.S. Pat. No. 3,189,612.

The second process, also illustrated in Scheme 1, consists in cyclizing an acid intermediate (IX), in the presence of a catalyst and according, for example, to the so-called Friedel-Crafts acylation reaction, in order to obtain the compound (I.a). Such intermediates (IX) used in this reaction are known and may be prepared, in particular, according to the method described in U.S. Pat. No. 4,564,641.

The third process, which is the preferred one, involves an oxidation reaction on an intermediate amino alcohol (II) to obtain the compound (I.a). More specifically, the implementation of this preferred preparation process presented at iii) in Scheme 1 consists: in oxidizing the hydroxyl function of the secondary amino alcohol (II) with a suitable reagent chosen from the group of those proposed for carrying out these oxidations, which are described, for example, in "Advanced Organic Chemistry" M. MARCH, 3rd Edition, p. 1057-1060. The reaction is favorably carried out using manganese derivatives such as potassium permanganate ($KMnO_4$) and manganese dioxide ($MnO_2$), or chromium derivatives such as chromium trioxide ($CrO_3$), the $CrO_3$-pyridine complex, pyridinium dichromate and pyridinium chlorochromate, which is the preferred reagent. With this reagent, the reaction is performed in an inert solvent which may be chosen from ethereal solvents such as diethyl ether, methyl t-butyl ether, diisopropyl or dibutyl ethers, tetrahydrofuran (THF) and 1,4-dioxane, or nitrobenzene, pyridine or halogenated hydrocarbons comprising 1 to 6 carbon atoms and among which methylene chloride is preferred, and consists, in the manner which is preferred, in reacting 1.5 to 4 moles of pyridinium chlorochromate per mole of compound (II) at a temperature of between 15° and 100° C., depending on the solvent, for 15 to 30 hours. More specifically, the method consists in adding, at a temperature of between 20° and 35° C., one mole of compound (II) dissolved in methylene chloride to 2.4 to 2.8 moles of the oxidizing reagent. At this temperature, the reaction is usually complete after 20 to 25 hours, and the compound of the invention (I.a) resulting from the oxidation is isolated and purified by standard methods which are described in the experimental part.

The preparation of the intermediate compound (II), which is the direct precursor employed in this preferred process, is illustrated in Scheme 3, Generally speaking, the amides (III), which are new products, are obtained in reacting a secondary amine (XI) of formula

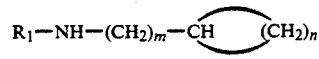

(XI)

in which $R_1$ is lower alkyl, with an acid chloride, prepared from the precursor acid (IV) and thionyl chloride and under the conditions of the invention, the amine is generally dissolved in a solvent which is inert to the reducing agent used, methylene chloride being preferred, or alternatively in reacting the precursor acide (IV) with an amine (XI) in an inert solvent such as methylene chloride and in the presence of a carbodiimide such as dicyclohexylcarbodiimide (DCCI) or 1-[N,N-dimethyl-(3-aminopropyl)]-3-ethyl-carbodiimide which are the preferred condensing agents.

The intermediate amide (III) thereby obtained is dissolved in a solvent which is inert to the reactants used, and is then reduced with a suitable reducing agent to give the amino alcohol (II) obtained as a mixture of isomers which are not separated. The reducing agents used for carrying out this intermediate step are chosen from the class of metal or organometallic hydrides, more specifically the hydrides derived from boron ($BH_3$) and the hydrides derived from aluminum, among which there may be mentioned, as examples, simple aluminum hydrides such as $AlH_3$ or Dibal [$(CH_3)_2CHCH_2]_2AlH$ and mixed hydrides of aluminum and alkali metals such as sodium or lithium, lithium aluminum hydride ($LiAlH_4$ or LAH) being preferred.

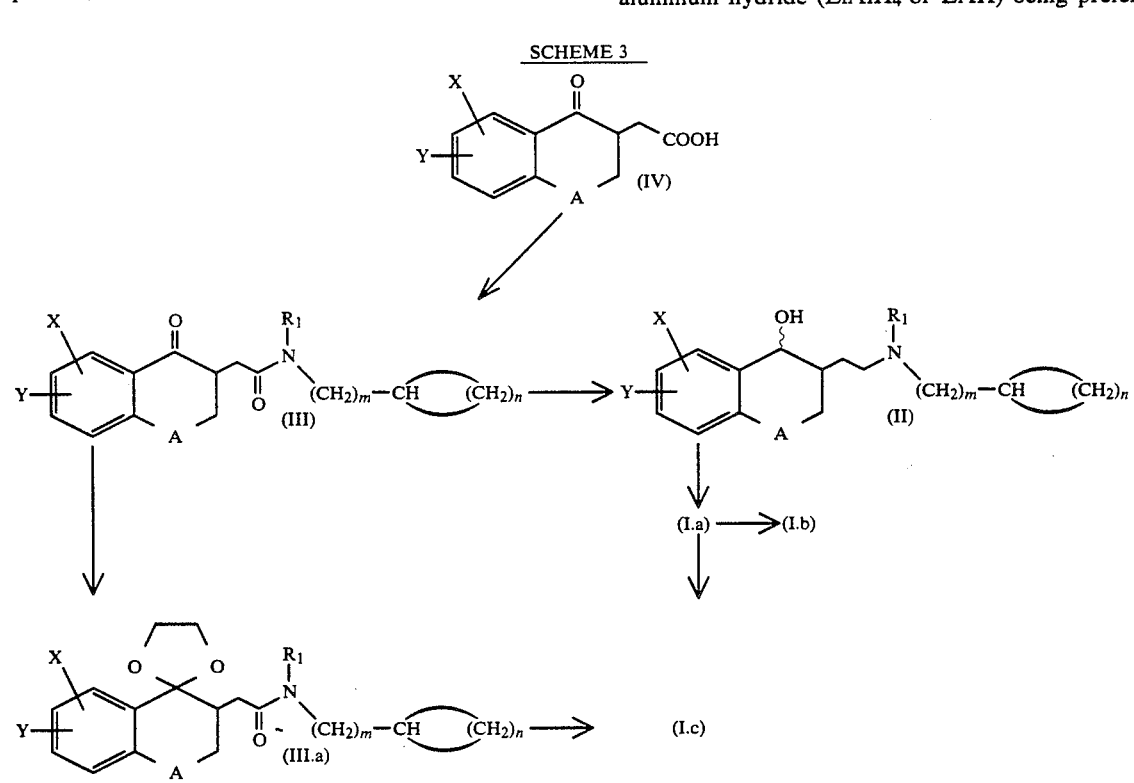

SCHEME 3 and consists in starting from an acid (IV), and in preparing from it the amide (III) which is then reduced to obtain the alcohol (II).

As shown in Scheme 3, amides (III.a) are obtained by condensing intermediates (III) with ethylene glycol in the presence of an acid catalyst such as p-toluenesulfonic acid. Also alcohols (II) in which $R_1$ is hydrogen are advantageously N-methylated by reductive alkylation with formaldehyde and formic acid, to prepare the corresponding N-methylated derivatives.

The acids (IV) are known and, if not marketed, are prepared according to described processes such as those published in J. Am. Chem. Soc. 1954, 76, p.4588; J. Agric. Food Chem. 1984, 32, p. 1125–1129; Chem. Pharm. Bull. 1987, 35, p. 1790–1795, or also according to the method proposed by C. C. Chan and P. S. Farmer, Pharmazie (1986), 41 (12), 835–836. Amines (XI) are available on the market, particularly those in which $R_1$ is hydrogen. When $R_1$ is lower alkyl, the secondary amines (XI) are known, and may be prepared according to methods described in the state of the art, or alternatively according to the method proposed by F. F. Blicke, E. Monroe, J. Amer. Chem. Soc., 1939(61), p. 91–95.

The present invention is illustrated without implied limitation by the examples which follow. The state of purity, the physicochemical characteristics and the structural identity of the products are determined and reported as follows:

the products are purified by suitable techniques, in particular by column chromatography for which the so-called "Chromatoflash" technique on a column of silica ("Merck" brand, product Kieselgel H 60, particle size 230 to 400 mesh) is favorably used. The state of purity of the products obtained is determined by the method of thin-layer chromatography (TLC) on silica ("Merck" ready-to-use plates); the Rf values observed together with the references to the elution solvents used are shown in the examples.

the physicochemical characteristics of the products are represented by:

a) the melting point, determined by the capillary tube method, and the value of which as shown is not corrected b) the infrared (IR) spectrography of the compounds in KBr disks; the most intense absorptions are reported by their wavenumber value in $cm^{-1}$.

the structural identity of the products is determined in accordance with:

a) the proton nuclear magnetic resonance (NMR) studied at 90 MHz, the products being solubilized in deterochloroform in the presence of trace amounts of sodium hydroxide when a compound is studied as a salt, most often as an hydrochloride. The appearance of the signals and their chemical shift expressed in ppm relative to tetramethylsilane used as internal reference are shown. Protons termed exchangeable after addition of deuterium oxide are also indicated.

b) the elemental percentage analysis, the results of which, complying with accepted norms, are not reported, but are indicated as being performed by showing the elements assayed.

EXAMPLE 1

2-[2-[(N-Cyclopropylmethyl-N-Methyl)Amino]Ethyl]-1-Oxo-1,2-Dihydroindene Hydrochloride (Formula I.a; $X=Y=H$; $R_1=CH_3$; $A=$Valency bond; $m=1$; $n=2$)

Stage 1: N-cyclopropylmethyl-N-methyl-2-[2-(1-oxo-1,2-dihydroindenyl)]-acetamide (III; $X=Y=H$; $R_1=CH_3$; $A=$valency bond; $m=1$; $n=2$)

a) 70 ml of anhydrous methylene chloride, to which 6.8 g (35.7 mmol) of (1-indanone)-2-acetic acid are added, are introduced into a 250-ml reactor set up in the reflux position and kept protected from moisture by a calcium chloride guard tube, and under a nitrogen atmosphere.

A solution of 9.9 g (6.1 ml–83.0 mmol) of thionyl chloride in 70 ml of anhydrous methylene chloride is added dropwise and with stirring in the course of 15 minutes to the suspension obtained.

After this introduction, the suspension is heated to reflux for one hour. The orange-colored solution obtained is evaporated under vacuum and on a water bath. An orange-colored oily residue is obtained, consisting of the crude acid chloride, which is employed in the next step without further treatment.

b) 10.0 g (120.0 mmol) of N-(cyclopropylmethyl)-methylamine, dissolved in 70 ml of anhydrous THF (tetrahydrofuran), are introduced into a 500-ml reactor set up in the reflux position with a calcium chloride guard tube and under a nitrogen atmosphere, and 70 ml of anhydrous methylene chloride are then added. The acid chloride prepared in stage 1a) above, dissolved in 110 ml of anhydrous methylene chloride, is added dropwise and with stirring in the course of 15 minutes and at a temperature of between 25° and 30° C.

The orange-colored solution obtained is heated on an oil bath to reflux, which is maintained for 2 hours. After cooling to 20°–25° C., the solution is extracted successively with:

50 ml of saturated $NaHCO_3$ solution
50 ml of N HCl solution
twice 50 ml of water.

The organic phase is dehydrated over $Na_2SO_4$, and the solvents are then removed by distillation under vacuum and on a water bath at 50° C.

An oily residue of 8.0 g is obtained, which is purified by "Chromatoflash".

Elution with ethyl acetate enables 5.6 g of purified N-cyclopropylmethyl-N-methyl-2-[2-(1-oxo-1,2-dihydroindenyl)]-acetamide to be obtained. Yld=60.9%

TLC: Rf=0.70 (ethyl acetate)

Stage 2: 2-[2-[(N-cyclopropylmethyl-N-methyl-)amino]ethyl]-1-hydroxy-1,2-dihydroindene (isomers II ; $X=Y=H$ ; $R_1=CH_3$; $A=$valency bond; $m=1$; $n=2$)

55 ml of anhydrous diethyl ether and 3.1 g (81.6 mmol) of lithium aluminum hydride (LAH) are introduced into a 250-ml reactor set up in the reflux position with a calcium chloride guard tube and under a nitrogen atmosphere.

A solution of 5.6 g (21.8 mmol) of the amide obtained in stage 1b) above, dissolved in 55 ml of ether, is added dropwise and with stirring in the course of 15 minutes to the suspension obtained.

The introduction is exothermic and ends with the ether refluxing. The mixture is then heated on an oil bath to maintain this reflux for 2 hours.

To the gray suspension which is cooled to a temperature below 10° C., the following are successively added dropwise and cautiously:

3.1 ml of water,
3.1 ml of 15% (W/v) NaOH solution
7.0 ml of water.

The white suspension obtained is kept stirring at room temperature for one and a half hours, and the insoluble matter is then filtered off on a Büchner and washed with ether.

The ether phases are combined and evaporated under vacuum on a water bath at 50° C.

4.5 g of residual crude product are obtained, which takes the form of a colored oil which is purified by "Chromatoflash".

Elution with a mixture of methylene chloride and methanol containing 10% of ammonia solution (95:5 v/v) enables the product to be purified in the form of a yellow oil, consisting of a mixture of isomers.

Weight: 4.0 g Yld=74.9%

TLC: Rf=0.30 and 0.50 (preponderant) (methylene chloride/methanol, 10% NH$_4$OH-95:5 v/v).

Stage 3: 2-[2-[(N-cyclopropylmethyl-N-methyl)amino]ethyl]-1-oxo-,1,2-dihydroindene (I.a; X=Y=H; R$_1$=CH$_3$; A=valency bond; m=1; n=2)

4.0 g (16.3 mmol) of the mixture of isomers of amino alcohols prepared in stage 2 above and 190 ml of anhydrous methylene chloride are introduced in a round-bottomed flask. 9.25 g (43.0 mmol) of pyridinium chlorochromate are added with stirring.

The blackish mixture obtained is kept stirring for 16 hours at 20°-25° C. After standing, the supernatant methylene chloride phase is decanted, and the residual gum is treated again with methylene chloride, which is also decanted. The combined organic phases are filtered through infusorial earth and then extracted with twice 100 ml of N NaOH solution.

The alkaline phase is discarded and 250 ml of ether are added to the organic phase. The precipitate which forms is filtered off in infusorial earth and the filtrate concentrated under vacuum on a water bath at 50° C. The residue is taken up with 150 ml of hexane, the insoluble matter is filtered off and the filtrate is extracted twice with twice 25 ml of 10% (v/v) HCl solution.

The organic phase is discarded and the acid phase is alkalinized to pH 12 at a temperature in the region of 10° C. with 10N NaOH solution.

The alkaline mixture is extracted with three times 50 ml of ether. The combined ether phases are washed with water and then dehydrated over Na$_2$SO$_4$. The ether is removed by distillation under vacuum on a water bath at 50° C. The product is obtained in the form of a colorless oil in a satisfactory state of purity after examination in TLC.

Weight: 3.5 g Yld=88.2%

TLC: Rf=0.25-0.40 (methylene chloride/methanol, 10% NH$_4$OH - 95:5 v/v).

Preparation of the Hydrochloride

The amino ketone obtained above is solubilized in 35 ml of anhydrous methylene chloride. Approximately 5 ml of approximately 5N ethereal hydrogen chloride are added at 10° C., and the solvents are then driven of by distillation under vacuum and on a water bath at 50° C. The residue is dissolved in 20 ml of isopropanol. 50 ml of ether are added to precipitate the hydrochloride. The insoluble matter is filtered off, washed with ether and dried under vacuum. Weight=3.5 g.

The product is taken up for purification with 15 ml of isopropanol in 25 ml of ether. The insoluble matter is filtered off, washed with ether and then dried.

Weight: 3.0 g Yld=74.6% M.p.=160°-162° C.

TLC: Rf=0.30-0.40 (methylene chloride/methanol, 10% NH$_4$OH - 95:5 v/v).

Analysis (C$_{16}$H$_{22}$ClNO) C, H, Cl, N, O

IR (KBr): 2900, 2500, 1710, 1610, 1460, 1204, 1020, 750 cm$^{-1}$.

NMR: 0-0.2 (m, 2H); 0.3-0.6 (m, 2H); 0.6-1 (m, 1H); 1.3-3.5 (m, 9H); 2.3 (s, 3H); 7.2-7.8 (m, 4H)

EXAMPLE 2

2-[2-[(N-Cyclopropylmethyl-N-Methyl)Amino]Ethyl]-1-Oxo-1,2,3,4-Tetrahydronaphthalene Hydrochloride (Formula I.a; X=Y=H; R$_1$=CH$_3$; A=CH$_2$; m=1; n=2)

Stage 1: N-cyclopropylmethyl-N-methyl-2-[2-(1-oxo-1,2,3,4-tetrahydronaphthyl)]-acetamide (III; X=Y=H; R$_1$=CH$_3$; A=CH$_2$; m=1; n=2)

a) 320 ml of anhydrous methylene chloride, to which 30.6 g (150 mmol) of 1-oxo-1,2,3,4-tetrahydro-2-naphthalene-acetic acid are added, are introduced into a 1-liter reactor set up in the reflux position under a nitrogen atmosphere and protected from moisture by a calcium chloride guard tube.

The orange-colored solution obtained is stirred, and a solution of 41.5 g (25.3 ml-35 mmol) of thionyl chloride, dissolved in 320 ml of anhydrous methylene chloride, is then added dropwise in the course of 10 minutes.

After this introduction, the solution is heated on an oil bath and brought to reflux, which is maintained for one hour. The orange-colored solution obtained is first cooled and then evaporated under vacuum on a water bath at 50° C. A colored residue of 30.0 g is obtained, consisting of the crude acid chloride, which is employed in the next phase without further treatment.

b) 25.5 g (300.0 mmol) of N-(cyclopropylmethyl)-methylamine, dissolved in anhydrous THF, are introduced into a 1-liter reactor set up in the reflux position under a nitrogen atmosphere, and 450 ml of anhydrous methylene chloride are then added.

The acid chloride prepared above in stage 1a), dissolved in 320 ml of anhydrous methylene chloride, is added dropwise and with stirring in the course of 15 minutes and at room temperature.

The brown solution obtained is heated to reflux on an oil bath and kept refluxing for 3 hours. After cooling to room temperature, the mixture is washed with 250 ml of NaHCO$_3$ solution.

The supernatant organic phase is extracted with 250 ml of 10% HCl solution and then washed with 250 ml of water.

The organic phase is then dehydrated over Na$_2$SO$_4$, and the solvents are removed by distillation under vacuum and on a water bath at 50° C.

An (oily) residue of 39.0 g is obtained, which is purified by "Chromatoflash".

Elution with ethyl acetate enables 26.8 g of purified N-cyclopropylmethyl-N-methyl-2-[2-(1-oxo-1,2,-3,4-tetrahydronaphthyl)]-acetamide. Yld=65.9%

TLC: Rf=0.80 (ethyl acetate)

Stage 2: 2-[2-[(N-cyclopropylmethyl-N-methyl)amino]ethyl]-1-hydroxy-1,2,3,4-tetrahydronaphthalene. (isomers II; X=Y=H; R$_1$=CH$_3$; A=CH$_2$; m=1; n=2) 250 ml of anhydrous diethyl ether and 13.9 g (367.0 mmol) of lithium aluminum hydride (LAH) are introduced with stirring into a 1-liter reactor set up in the reflux position, protected from moisture by a calcium chloride guard tube and under a nitrogen atmosphere.

A solution of 26.8 g (98.8 mmol) of the amide obtained in stage 1b) above, dissolved in 250 ml of ether, is added dropwise and with stirring in the course of 30 minutes to the suspension obtained.

The introduction is exothermic and ends with the ether refluxing. The solution is then heated in an oil bath to maintain this reflux for 45 minutes.

To the suspension obtained which is cooled to a temperature below 0° C., the following are successively added dropwise and cautiously:

13.9 ml of demineralized water,
13.9 ml of 15% (w/v) NaOH solution
31 ml of demineralized water.

The suspension obtained is kept stirring for 30 minutes at 0° C., and the insoluble matter is then filtered off under vacuum on a Büchner coated with infusorial earth.

The filtrate is evaporated under vacuum on a water bath at 50° C.

The residual crude product obtained weighs 23.3 g, and is purified by "Chromatoflash".

Elution with a mixture of methylene chloride and methanol containing 10% of ammonia solution (95:5 v/v) enables the product to be purified in the form of a yellow oil, consisting of a mixture of isomers. Weight: 9.8 g Yld=38.2%

TLC: Rf=0.50–0.70 (methylene chloride/methanol, 10% NH$_4$OH 95:5 v/v).

Stage 3: 2-[2-[(N-cyclopropylmethyl-N-methyl)amino]ethyl]-1-oxo-1,2,3,4-tetrahydronaphthalene (I.a; $X=Y=H$; $R_1=CH_3$; $A=CH_2$; $m=1$; $n=2$)

9.7 g (37.4 mmol) of the mixture of isomers of amino alcohols prepared in stage 2 above, dissolved in 430 ml of anhydrous methylene chloride are introduced into a one liter reactor set up in the reflux position under a nitrogen atmosphere and protected from moisture by a calcium chloride guard tube. 21.2 g (98.0 mmol) of pyridinium chlorochromate are added with stirring.

The blackish mixture obtained is kept stirring for 20 hours at room temperature. The supernatant phase is decanted and filtered through infusorial earth. The residual gum is extracted with twice 150 ml of methylene chloride, which is decanted and filtered through infusorial earth. The organic phases are extracted successively with three times 150 ml of N NaOH solution and then with 150 ml of water. The aqueous phases are discarded and 500 ml of ether are added to the organic phase obtained. The precipitate which forms is filtered off on infusorial earth and the filtrate concentrated under vacuum on a water bath at 50° C. The residue obtained is taken up in 150 ml of hexane. The flocculent insoluble matter is filtered off and the filtrate containing the hexane phase is extracted with twice 75 ml of 10% HCl solution.

The organic phase is discarded and the acid phase in alkalinized to pH 12 in the cold state with NaOH solution.

The alkaline mixture is extracted with three times 100 ml of ether. The combined ether phases are washed with water and then dehydrated over Na$_2$SO$_4$. The ether is removed by distillation under vacuum on a water bath at 50° C. 7.7 g of 2-[2-[(N-cyclopropylmethyl-N-methyl)amino]ethyl]-1-oxo-1,2,3,4-tetrahydronaphthalene are obtained in the form of a purplish oil. Yld=80%

TLC: Rf=0.60 (methylene chloride/methanol, 10% NH$_4$OH - 80:20 v/v)

Preparation of the Hydrochloride

The amino ketone obtained above is solubilized in 80 ml of ether. After cooling of the solution, 12 ml of approximately 5N ethereal hydrogen chloride are added, and the solvents are driven off by distillation under vacuum on a water bath at 50° C. The violet-colored residue obtained is dissolved in 25 ml of isopropanol. 50 ml of ether are added to the hydrochloride, which precipitates slowly. After 48 hours of standing in the cold, the insoluble matter is filtered off, washed with ether and dried under vacuum.

Weight=7.0 g

The precipitate is taken up for purification with 25 ml of isopropanol and 50 ml of ether. The solution is left stirring for two hours in the cold, and the insoluble matter is filtered off, then washed with ether and dried under vacuum at 60° C. Weight=6.0 g Yld.=68.3% M.p.=123°–125° C.

TLC: Rf=0.50–0.65 (methylene chloride/methanol, 10% NH$_4$OH - 80:20 v/v)

Analysis (C$_{17}$H$_{24}$ClNO) C, H, Cl, N, O

IR (KBr): 2920, 2005, 1680, 1600, 1422, 1220, 1000, 740 cm$^{-1}$

NMR: 0–0.2 (m, 2H); 0.3–0.6 (m 2H); 0.6–1 (m, 1H); 2.3 (s, 3H); 1.3–3.1 (m 11H); 7.1–8.1 (m, 4H)

EXAMPLE 3

2-[2-[(N-Cyclobutylmethy-N-Methyl)Amino]Ethyl]1-oxo-1, 2, 3,4-Tetrahydronaohthalene Hydrochloride (Formula I.a; $X=Y=H$; $A=CH_2$; $R_1=CH_3$; $m=1$; $n=3$)

According to the procedure described in Example 2 above, starting from 1-oxo-1,2,3,4-tetrahydro-2-naphthalene-acetic acid and N-(cyclobutylmethyl)methylamine, the following compounds are obtained successively in stages 1 to 3.

Stage 1: N-cyclobutylmethyl-N-methyl-2-[2-(1-oxo-1,2,3,4-tetrahydronaphthyl)]-acetamide (III; $X=Y=H$; $A=CH_2$; $R_1=CH_3$; $m=1$; $n=3$) Yld 65.6%

TLC: Rf=0.80 (ethyl acetate)

Stage 2: 2-[2-[(N-cyclobutylmethyl-N-methyl)amino]ethyl]-1-hydroxy-1,2,3,4-tetrahydronaphthalene.

(isomers II; $X=Y=H$; $A=CH_2$; $R_1=CH_3$; $m=1$; $n=3$) Yld=91.5%

TLC: Rf=0.50; preponderantly 0.70 (methylene chloride/methanol, 10% NH$_4$OH - 95:5 v/v)

Stage 3: 2-[2-[(N-cyclobutylmethyl-N-methyl)amino]ethyl]-1-oxo-1,2,3,4-tetrahydronaphthalene (I.a; $X=Y=H$; $A=CH_2$; $R_1=CH_3$; $m=1$; $n=3$) Yld=83.9% (violet oil)

TLC: Rf=0.60 (methylene chloride/methanol, 10% NH$_4$OH - 95:5 v/v)

Hydrochloride

Yld=52.9% M.p.=120°–121° C.

TLC: Rf=0.40–0.60 (methylene chloride/methanol, 10% NH$_4$OH - 95:5 v/v)

Analysis (C$_{18}$H$_{26}$ClNO) C, H, Cl, N, O

IR (KBr): 2900, 2500, 1680, 1600, 1450, 1280, 1210, 1105, 740 cm$^{-1}$

NMR: 1.25–2.8 (m 15H); 2.2 (s, 3H); 2.85–3.20 (m, 2H); 7.1–8.1 (m, 4H)

EXAMPLE 4

2-[2-[(N-Cyclopropylethyl-N-Methyl)Amino]Ethyl]-1-oxo-1,2,3,4-Tetrahydronaphthalene Hydrochloride (Formula I.a; $X=Y=H$; $A=CH_2$; $R_1=CH_3$; $m=2$; $n=2$)

According to the procedure described in Example 2 above, starting from 1-oxo-1,2,3,4-tetrahydro-2-naphthalene-acetic acid and N-(cyclopropylethyl)methylamine, the following compounds are obtained successively in stages 1 to 3.

Stage 1

N-cyclopropylethyl-N-methyl-2-[2-(1-oxo-1,2, 3,4-tetrahydronaphthyl)]-acetamide (III; X=Y=H; A=CH$_2$; R$_1$=CH$_3$; m=2; n=2) Yld=64.8%

TLC: Rf=0.80 (ethyl acetate)

Stage 2: 2-[(N-cyclopropylethyl-N-methyl)amino]ethyl]-1-hydroxy-1,2,3,4-tetrahydronaphthalene (isomers II; X=Y=H; A=CH$_2$; R$_1$=CH$_3$; m=2; n=2) Yld=93%

TLC: Rf=0.20 (methylene chloride/methanol, 10% NH$_4$OH - 95:5 v/v)

Stage 3: 2-[2-[(N-cyclopropylethyl-N-methyl)amino]ethyl]-1-oxo-1,2,3,4-tetrahydronaphthalene (I.a; X=Y=H; A=CH$_2$; R$_1$=CH$_3$; m=2, n=2) Yld=73.4% (greenish oil)

TLC: Rf=0.60-0.70 (methylene chloride/methanol, 10% NH$_4$OH - 95:5 v/v)

Hydrochloride

Yld=44.1% M.p.=103°-106° C.

TLC: Rf=0.50 (methylene chloride/methanol, 10% NH$_4$OH - 95:5 v/v)

Analysis (C$_{18}$H$_{26}$ClNO) C, H, Cl, N, O

IR (KBr): 2900, 2800, 1680, 1600, 1450, 1360, 1210, 1005, 740 cm$^{-1}$

NMR: 0-0.1 (m, 2H); 0.4-0.5 (m, 2H); 0.5-0.8 (m, 1H); 1.2-2.7 (m, 11H); 2.8-3.1 (m, 2H); 7.1-8.1 (m, 4H)

EXAMPLE 5

2-[2-[(N-Cyclohexylmethyl-N-Methyl)Amino]-Ethyl]-1-Oxo-1,2,3,4-Tetrahydronaphthalene Hydrochloride Formule I.a; X=Y=H; R$_1$=CH$_3$; A=CH$_2$; m=1; n=5)

The compound is prepared according to the procedure described in Example 2 from 1-oxo-1,2,3,4-tetrahydro-2-naphthalene-acetic acid and N-cyclohexyl-methyl-methylamine.

Stage 1: N-cyclohexylmethyl-N-methyl-2-[2-(1-oxo-1,2,3,4-tetrahydronaphthyl)]-acetamide (III.a; X=Y=H; R$_1$=CH$_3$; A=CH$_2$ ; m=1; n=5) Yld.=53%

TLC : Rf=0.8 (yellow oil after ethyl-acetate chromatographic purification)

Stage 2: 2-[2-[(N-cyclohexylmethyl-N-methyl)amino]ethyl]-1-hydroxy-1,2,3,4-tetrahydronaphthalene.

(isomers II; X=Y=H; R$_1$=CH$_3$; A=CH$_2$; m=1; n=5) Yld.=83.5%

TLC : Rf=0.70 and 0.80 (methylene chloride/methanol, 10% NH$_4$OH - 95:5 v/v)

Stage3: 2-[2-[(N-cyclohexylmethyl-N-methyl)amino]-ethyl]-1-oxo-1,2,3,4-tetrahydronaphthalene (I.a; X=Y=H; A=CH$_2$; R$_1$=CH$_3$; m=1;n=5) Yld. 73.4% (greenish oil)

TLC : Rf=0.60-0.70 (methylene chloride/methanol, 10% NH$_4$OH - 95:5 v/v)

Hydrochloride

Yld. 80% M. p.=165° C.

TLC: Rf=0.25-0.45 (methylene chloride/methanol, 10% NH$_4$OH - 95:5 v/v)

Analysis: (C$_{20}$H$_{30}$ClNO) C, H, Cl, N, O

IR (KBr): 2900, 2400, 1680, 1600, 1440, 1220, 900, 740 cm$^{-1}$

NMR: 0.5-2.8 (m, 20H); 2.15 (s, 3H); 2.8-3.1 (m, 2H); 7.1-8.1 (m, 4H)

EXAMPLE 6

2-[2-[(N-Cyclohexylmethyl-N-Methyl)Amino]-Ethyl]6-Methoxy-1-oxo-1,2,3,4-Tetrahydronaphthalene Hydrochloride (Formula I.a ; X=6-OCH$_3$ ; Y=H ; R$_1$=CH$_3$; A=CH$_2$ ; m=1 ; n=5)

Stage 1: N-cyclohexylmethyl-N-methyl-2-[2-(6-methoxy-1-oxo-1,2,3,4-tetrahydronaphthyl)]-acetamide (III ; X=OCH$_3$; Y=H ; R$_1$=CH$_3$; A=CH$_2$ ; m=1; n=5) 60 ml of methylene chloride previously dehydrated on a molecular sieve are introduced in a reactor protected from moisture; then 1.00 g (4.3 mmol) of 1-oxo-6-methoxy-1,2,3,4-tetrahydro-2-naphthaleneacetic acid, 0.68 g (5.4 mmol) of N-cyclohexylmethyl-methylamine and 1.33 g (6.45 mmol) of dicyclohexylcarbodiimide (DCCI) are introduced.

After dissolution, the mixture is stirred for 1h30 at 20°-25° C., then extracted. 1.7 g of a crude product is obtained, which is taken up with 20 ml anhydrous ether. The insoluble matter is filtered off and discarded. The ethereal phase is purified by "Chromatoflash". Elution with a mixture of ethyl acetate and hexane (70:30) enables 0.70 g of purified product to be obtained. Yld.=47.5%

TLC: Rf=0.60-0.70 (ethyl acetate/hexane - 70:30 v/v)

Stage 2: 2-[2-[(N-cyclohexylmethyl-N-methyl)amino]-ethyl]-6-methoxy-1-hydroxy-1,2,3,4-tetrahydronaphth (isomers II; X=6-OCH$_3$; Y=H; R$_1$=CH$_3$; A=CH$_2$; m=1; n=5)

Prepared from the product obtained in the previous stage and according to the procedure described in Example 2 - Stage 2. Yld.=92.1%

TLC: Rf=0.15-0.40 (methylene chloride/methanol, 10% NH$_4$OH - 97:3 v/v)

Stage 3: 2-[2-[(N-cyclohexylmethyl-N-methyl)amino]-ethyl]-6-methoxy-1-oxo-1,2,3,4-tetrahydronaphalene Prepared according to the procedure described in Example 2 - Stage 3. Yld.=73.%

TLC: Rf=0.20-0.30 (methylene chloride/methanol, 10% NH$_4$OH - 97:3 v/v)

Hydrochloride

Yld. 73% M. p.=172° C.

TLC: Rf=0.25 (methylene chloride/methanol, 10% NH$_4$OH 97:3 v/v)

Analysis (C$_{21}$H$_{32}$ClNO$_2$) C, H, Cl, N, O

IR (KBr): 2900, 2550, 1675, 1600, 1440, 1250, 1100, 840, 760 cm$^{-1}$

NMR: 0.6-2.7 (m, 20H); 2.2 (s, 3H; 2.8-3.1 (m, 2H); 3.8 (s, 3H); 6.6-6.9 (m, 2H); 8.0 (d, 1H)

EXAMPLE 7

2-[2-(N-Cyclopropylamino)Ethyl]-1-Oxo-1,2,3,4-Tetrahydronaphthalene (Formula I.a; X=Y=H; R$_1$=H; A=CH$_2$; m=0; n=2)

Stage 1: N-cyclopropyl-2-[2-(1-oxo-1,2,3,4-tetrahydronaphthyl)]-acetamide (III; X=Y=H; R$_1$=H; A=CH$_2$; m=0; n=2)

The compound is prepared according to the procedure described in Example 6 - Stage 1 above, starting from 1-oxo-1,2,3,4-tetrahydro-2-naphthalene-acetic acid and cyclopropylamine.

Yld.=86%

TLC: Rf=0.10–0.20 (ethyl acetate/hexane-70:30 v/v))

Stage 2: 2-[2-(N-cyclopropylamino)ethyl]-1-hydroxy-1,2,3,4-tetrahydronaphthalene (isomers II; $X=Y=H$; $R_1=H$; $A=CH_2$; $m=0$; $n=2$)

Prepared from the compound obtained at the previous stage and according to the procedure described in Example 2 - Stage 2.

Yld.=80%

TLC: Rf=0.20–0.30 (methylene chloride/methanol, 10% $NH_4OH$ - 95:5 v/v)

Stage 3: 2-[2-(N-cyclopropylamino)ethyl]-1-oxo-1,2,3,4-tetrahydronaphthalene (I.a; $X=Y=H$; $R_1=H$; $A=CH_2$; $m=0$; $n=2$)

Prepared according to the procedure described in Example 2 - Stage 3

Yld.=14.0% (unstable)

TLC: Rf=0.15–0.25 (methylene chloride/methanol, 10% $NH_4OH$ - 90:10 v/v)

Analysis ($C_{15}H_{19}NO$) C, H, N, O

IR (KBr): 2900, 2850, 1680, 1600, 1450, 1280, 1220, 1030, 740 cm$^{-1}$

NMR: 0.0–0.1 (m, 2H); 0.2–0.6 (m, 3H); 1.65–2.35 (m, 5H); 2.5–3.25 (m, 5H with 1 exch.); 7.1–7.6 (m, 3H); 7.9–8.1 (m, 1H)

EXAMPLE 8

2-[2-[(N-Cyclopropyl-N-Methyl)Amino]Ethyl]-1-Oxo-1,2,3,4-Tetrahydronaphthalene Hydrochloride (Formula I.a; $X=Y=H$; $R_1=CH_3$; $A=CH_2$; $m=0$; $n=2$)

Stage 1: 2-[2-[(N-cyclopropyl-N-methyl)amino]ethyl]-1-hydroxy-1,2,3,4-tetrahydronaphthalene (Isomers II; $X=Y=H$; $R_1=CH_3$; $A=CH_2$; $m=0$; $n=2$)

a) 15.0 g (65.2mmol ) of the amine obtained in Example 7 - Stage 2 above are introduced into a round-bottomed flask. 9.4 g (196 mmol) pure formic acid are then added with cooling, then 13.3 g of an aqueous formaldehyde solution (37% w/v). The mixture is stirred for 24 h at 80° C. and then cooled.

19.6 ml of a 1N HCl solution are added. After extractions with three times 30 ml of ether, the aqueous phase is alkalinized at room temperature with 10N NaOH solution, followed by extraction with ether. The solvent is then evaporated and the product is obtained in the form of an oil (Yld.: 92%). The product is purified by chromatography on a silica column by selective elution with ethyl acetate.

Yld.=72%

TLC: Rf=0.35–0.50 (ethyl acetate)

Stage 2: 2-[2-[(N-cyclopropyl-N-methyl)amino]ethyl]-1-oxo-1,2,3,4-tetrahydronaphthalene (I.a; $X=Y=H$; $R_1=CH_3$; $A=CH_2$; $m=0$; $n=2$)

Prepared from the product obtained in Stage 1above and according to the procedure described in Example 2 - Stage 3. Yld.=67%

TLC: Rf=0.70–0.90 (methylene chloride/methanol, 10% $NH_4OH$ - 95:5 v/v)

Hydrochloride

Yld.=77% M.p.=167–169° C.

TLC: Rf=0.65–0.75 (methylene chloride/methanol, 10% $NH_4OH$ - 95:5 v/v)

Analysis ($C_{16}H_{21}ClNO$) C, H, Cl, N, O

IR (KBr): 2900, 2600, 2450, 1675, 1600, 1410, 1220, 1030, 740 cm$^{-1}$

NMR: 0.2–0.55 (m, 4H); 1.35–2.8 (m, 8H); 2.35 (S, 3H); 2.85–3.1 (m, 2H); 7.1–7.6 (m, 3H); 7.9–8.15 (m, 1H)

EXAMPLE 9

2-[2-[(N-Cyclopropylmethyl-N-Propyl)Amino]Ethyl]-1-oxo-1,2,3,4-Tetrahydronaphthalene Hydrochloride (Formula I.a; $X=Y=H$; $R_1=nC_3H_7$; $A=CH_2$; $m=1$; $n=2$)

Stage 1: N-cyclopropylmethyl-N-propyl-2-[2-(1-oxo-1,2,3,4-tetrahydronaphthyl)]-acetamide (III; $X=Y=H$; $R_1=C_3H_7$; $A=CH_2$; $m=1$; $n=2$)

The compound is prepared as described in Example 6 - stage 1 above, from 1-oxo-1,2,3,4-tetrahydro-2-naphthalene-acetic acid and N-cyclopropylmethyl-propylamine.

The crude product obtained is purified by column chromatography using a mixture of ethyl acetate and hexane as elution solvent.

Yld.=65%

TLC: Rf=0.60–0.65 (ethyl acetate/hexane - 70:30 v/v)

Stage 2: 2-[2-[(N-cyclopropylmethyl-N-propyl)amino]ethyl]-1-hydroxy-1,2,3,4-tetrahydronaphthalene (isomers II; $X=Y=H$; $R_1=nC_3H_7$; $A=CH_2$; $m=1$; $n=2$)

Prepared from the product obtained in the previous stage and according to the procedure described in Example 2 - Stage 2.

TLC: RF=0.10–0.50 (methylene chloride/methanol, 10% - 95:5 v/v)

Stage 3: 2-[2-[(N-cyclopropylmethyl-N-propyl)amino]ethyl]-1-oxo-1,2,3,4-tetrahydronaphthalene (I.a; $X=Y=H$; $R_1=nC_3H_7$; $A=CH_2$; $m=1$; $n=2$)

Prepared according to the procedure described in Example 2 - Stage 3. The product obtained is purified by column chromatography using a mixture of methylene chloride and methanol, 10% $NH_4OH$ as elution solvent.

Yld.=55.0%

TLC: RF=0.30–0.60 (methylene chloride/methanol, 10% $NH_4OH$ - 95:5 v/v)

Hydrochloride

Yld.=60% M.p.=98°–100° C.

TLC: Rf=0.40 (methylene chloride/methanol, 10% $NH_4OH$ - 95:5 v/v)

Analysis ($C_{19}H_{28}ClNO$) C, H, Cl, N, O

IR (KBr): 2900, 2450, 1670, 1600, 1470, 1450, 1270, 1220, 730 cm$^{-1}$

NMR: 0.0–0.2 (m, 2H); 0.3–0.6 (m, 2H); 0.6–1.0 (m, 4H); 1.1–2.8 (m, 13H); 2.8–3.15 (m, 2H); 7.1–7.6 m, 3H); 7.9–8.2 (m, 1H)

EXAMPLE 10

2-[2-[(N-Cyclopropylmethyl-N-Methyl)Amino]Ethyl]-1-Benzosuberone Hydrochloride (Formula I.a; $X=Y=H$; $R_1CH_3$; $A=CH_2-CH_2$; $m=1$; $n=2$)

The compound is prepared from 2-(1-benzosuberone)-acetic acid and N-cyclopropylemethylmethylamine according to the procedure described in Stages 1-3 of Example 2.

Stage 1: N-cyclopropylmethyl-N-methyl-2-[(1-benzosuberone)-2-yl]-acetamide (III; X=Y=H; R$_1$=CH$_3$; A=CH$_2$—CH$_2$; m=1; n=2)

Yld.=42.8%

TLC: Rf=0.80 (oil after chromatographic purification using ethyl acetate)

Stage 2: 2-[2-[(N-cyclopropylmethyl-N-methyl)amino]ethyl]-1-benzosuberol (isomers II; X=Y=H; R$_1$=CH$_3$; A=CH$_2$—CH$_2$; m=1; n=2)

Yld=80.1%

TLC: Rf=0.60–0.65 (methylene chloride/methanol, 10% NH$_4$OH - 95:5 v/v)

Stage 3: 2-[2-[(N-cyclopropylmethyl-N-methyl)amino]ethyl]-1-benzosuberone (I.a; X=Y=H; R$_1$=CH$_3$; A=CH$_2$—CH$_2$; m=1; n=2) Yld.=75.6%

TLC: Rf=0.70–0.80 (methylene chloride/methanol, 10% NH$_4$OH - 95:5 v/v)

Hydrochloride

Yld.=55% M.p.=97°–99° C.

TLC: Rf=0.50–0.60 (methylene chloride/methanol, 10% NH$_4$OH - 95:5 v/v)

Analysis (C$_{18}$H$_{26}$ClNO) C, H, Cl, N, O

IR (KBr): 2900, 2590, 2500, 1670, 1600, 1440, 1280, 1100, 960, 740 cm$^{-1}$

NMR: 0–0.15 (m, 2H); 0.3–0.6 (m, 2H); 0.6–0.9 (m, 1H); 1.4–2.5 (m, 11H); 2.3 (s, 3H); 2.8–3.1 (m, 2H) 7.1–7.7 (m, 4H)

EXAMPLE 11

2-[2-[(N-Cyclohexylmethyl-N-Methyl)Amino]-Ethyl]-1-Benzosuberone Hydrochloride (Formula I.a; X=Y=H; R$_1$=CH$_3$; A=CH$_2$—CH$_2$; m=1; n=5)

Prepared as described in Example 10 above from 2-(1-benzosuberone)acetic acid and N-cyclohexylmethyl-methylamine.

Stage 1: N-cyclohexylmethyl-N-methyl-2-[(1-benzosuberone)-2-yl]-acetamide (III; X=Y=H; R$_1$=CH$_3$; A=CH$_2$—CH$_2$; m=1; n=5)

Yld.=89.9%

TLC: Rf=0.70 (methylene chloride/methanol, 10% NH$_4$OH - 95:5 v:v)

Stage 2: 2-[2-[(N-cyclohexylmethyl-N-methyl)amino]ethyl]-1-benzosuberol (isomers II; X=Y=H; R$_1$=CH$_3$; A=CH$_2$—CH$_2$; m=1; n=5)

Yld.=95.2%

TLC: Rf=(0.30–0.40) (methylene chloride/methanol - 99:1 v/v)

Stage 3: 2-[2-[(N-cyclohexylmethyl-N-methyl)amino]ethyl]-1-benzosuberone (I.a; X=Y=H; R$_1$=CH$_3$; A=CH$_2$—CH$_2$; m=1; n=5) Yld.=73.9%

TLC: Rf=0.40–0.50 (methylene chloride/methanol - 99:1 v/v)

Hydrochloride

Yld. =92.8% M.p.=138°–140° C.

TLC: Rf=0.45 (methylene chloride/methanol - 99:1 v/v)

Analysis (C$_{21}$H$_{32}$ClNO) C, H, Cl, N, O

IR (KBr): 2900, 2600, 1675, 1600, 1440, 1280, 720 cm$^{-1}$

NMR: 0.6–2.5 (m, 22H); 2.2 (s, 3H); 2.8–3.1 (m, 2H); 7.0–7.7 (m, 4H)

EXAMPLE 12

2-[2-[(N-Cyclopropylmethyl-N-Methyl)Amino]-Ethyl]-1-[Spiro(Cyclodioxyethyl)]1,2,3,4-Tetrahydronaphthale (Formula I.c; X=Y=H; R$_1$=CH$_3$; A=CH$_2$; m=1; n=2)

Stage 1: N-cyclopropylmethyl-N-methyl-2-[2-[1-[spiro(cyclodioxyethyl)]-1,2,3,4-tetrahydronaphthyl]]-acetamide (III.a; X=Y=H; R$_1$=CH$_3$; A=CH$_2$; m=1; n=2)

6.6 g (24.3 mmol) of N-cyclopropylmethyl-N-methyl-2-(1-oxo-1,2,3,4-tetrahydronaphthyl)-acetamide as prepared in Example 2 - Stage 1, 29.7 ml of ethylene glycol, and 0.22 g of p-toluenesulfonic acid are dissolved in 260 ml of toluene in a reactor equipped with a cooling system, set up in the reflux position, and equipped with a Dean Starck separating system to remove the water formed.

The mixture is heated to reflux with elimination of the water formed. Progress is followed by gas chromatography. After 40 h refluxing, 27 ml water have been removed and GC indicates a progress of 80% product formed.

The solution is cooled, extracted with 150 ml of a NaHCO$_3$ satured solution, then washed with two times 150 ml of water.

The organic phase is dehydrated over Na$_2$SO$_4$, and the solvent is then evaporated.

A greeny oily residue of 7.0 g is obtained, which is purified by "Chromatoflash". Elution with an ethyl acetate/hexane mixture enables 3.6 g of purified product to be obtained.

Yld.=47,0%

TLC: Rf=0.40–0.50 (ethyl acetate)

Stage 2: 2-[2-[(N-cyclopropylmethyl-N-methyl)amino]ethyl]-1-[spiro(cyclodioxyethyl)]-1,2,3,4-tetrahydro naphhtalene (I.c ; X=Y=H; R$_1$=CH$_3$; A=CH$_2$; m=1; n=2)

The amide is dissolved in ether and reduced by lithium aluminum hydride according to the usual procedure.

Yld.=90.6%

TLC: Rf=0.50 (methylene chloride/methanol, 10% - NH$_4$OH - 95:5 v/v)

Analysis (C$_{19}$H$_{27}$NO$_2$) C, H, N, O

IR (KBr): 2900, 2800, 1450, 1290, 1060, 940, 760 cm$^{-1}$

NMR: 0.1–0.2 (m, 2H); 0.3–0.6 (m, 2H); 0.6–1.0 (m, 1H); 1.0–2.6 (m, 9H); 2.3 (s, 3H); 2.6–2,9 (m, 2H); 3.9–4.2 (m, 4H); 6.9–7.5 (m, 4H)

EXAMPLE 13

2-[2-[(N-Cyclobutylmethyl-N-Methyl)Amino]Ethyl]-1-Hydroxyimino-1,2,3,4Tetrahydronaphthalene (Formula I.b; V$_1$-V$_2$=NOH; X=Y=H; R$_1$=CH$_3$; A=CH$_2$; m=1; n=3) 0.90 g (3,3 mmol) of 2-[2-[(N-cyclobutylmethyl-N-methyl)amino]ethyl]-1-oxo-1,2,3,4-tetrahydronaphthalene. (Example 3 - Stage 3), 0.69 g (10,0 mmol) of hydroxylamine hydrochloride, 50 ml of anhydrous pyridine and 5.0 ml of absolute ethanol are introduced into a reactor. The mixture is stirred and heated, and the resulting solution is kept refluxing for 2 hours.

Then the solvents are removed by distillation under vacuum.

The residue is taken up by 50 ml of water. The mixture is alkalinized to pH 12 with 10N NaOH solution. The precipitate which forms is filtered off, washed with ether and then dried at 50° C. under vacuum. Weight=0.30 g Yld.=31.8% M.p.=120°-122° C.

TLC: Rf0.50 (methylene chloride/methanol, 10% NH₄OH - 95/5 v/v)

Analysis ($C_{18}H_{26}N_2O$) C, H, N, O

IR (KBr): 2900, 1490, 1460, 1440, 1160, 1060, 1000, 960, 760 cm$^{-1}$

NMR: 1.5-3.7 (m, 19H); 2.2 (s, 3H); 7.0-8.1 (m, 4H)

EXAMPLE 14

3-[2-[(N-Cyclopropylmethyl-N-Methyl)Amino]-Ethyl]4-Chromanone Hydrchloride (Formula I.a; X=Y=H; $R_1$=CH$_3$; A=0; m=1; n=2)

The product is prepared according to the procedure of Example 2- Stages 1 to 3 from 2-(4-chromanone)acetic acid and N-cyclopropylmethyl-methylamine.

Stage 1 : N-cyclopropylmethyl-N-methyl-2-[(4-chromanone)-3-yl]-acetamide (III; X=Y=H; $R_1$=CH$_3$; A=0; m=1; n=2)

Yld.=39,1%

TLC: Rf=0.30-0.40 (ethyl acetate/hexane - 70:30 v/v)

Stage 2: 3-[2-[(N-cyclopropylmethyl-N-methyl)amino]ethyl]-4-chromanol.

(isomers II; X=Y=H; $R_1$=CH$_3$; A=0; m=1; n=2)

Yld. =98.2%

TLC: Rf=0.40-0.50 (methylene chloride/methanol, 10% NH₄OH - 95:5 v/v)

Stage 3: 3-[2-[(N-cyclopropylmethyl-N-methyl)amino]ethyl]-4-chromanone (I.a; X=Y=H; $R_1$=CH$_3$; A=0; m=1; n=2)

Yld.=68.0%

TLC: Rf=0/40-0.50 (methylene chloride/methanol, 10% NH₄OH - 95:5 v/v)

Hydrochloride

Yld.=77.1% M.p.=170°-172° C.

TLC: Rf=0.45 (methylene chloride/methanol, 10% NH₄OH - 95:5 v/v)

Analysis ($C_{16}H_{22}ClNO_2$) C, H, Cl, N, O

IR (KBr): 2950, 2400, 1680, 1600, 1480, 1300, 1220, 1030, 820, 740 cm$^{-1}$

NMR: 0.05-0.4 (m, 2H); 0.4-0.6 (m, 2H); 0.65-1.0 (m, 1H); 1.4-1.8 (m, 1H); 1.9-3.0 (m, 6H); 2.35 (s, 3H); 4.1-4.7 (m, 2H); 6.85-7.95 (m, 4H)

EXAMPLE 15

3-[2-(N-Cyclohexylmethyl-N-Methyl)Amino]-Ethyl[-4-Chromanone Hydrochloride (Formula I.a; X=Y=H; $R_1$=CH$_3$; A=0; m=1; n=5)

Stage 1: N-cyclohexylmethyl-N-methyl-2-[(4-chromanone)-3-yl]-acetamide (III; X=Y=H; $R_1$=CH$_3$; A=0; m=1; n=5) 250 ml of methylene chloride previously dehydrated on molecular sieve are introduced in a reactor protected from moisture, then 15.05 g (73 mmol) of 2-(4-chromanone)-acetic acid and 11.55 g (90 mmol) of N-cyclohexylmethyl-methylamine hydrochloride are introduced.

A solution of 20.85 g (109 mmol) of 1-[(3-dimethylamino)-propyl]-3-ethyl-carbodiimide in 100 ml methyle chloride is added, with stirring and at 25° C. The solution is kept stirring for 2 hours at 20°-25° C., then successively extracted with 100 ml of a 1N HCl solution, two times 100 ml of water, then 100 ml of a satured NaHCO₃ solution, and finally two times 100 ml of water.

After dehydration over Na₂SO₄, the methylene chloride is evaporated by distillation under vacuum.

The crude residue is a yellow oil (22.5 g) which is purified by chromatography on a silica column - Elution with a mixture of acetone and ethyl acetate (70:30 v/v) enables 18.85 g of pure product to be obtained.

Yld.=85.%

TLC: Rf=0.90-0.95 (ethyl acetate)

Stage 2: 3-[2-[(N-cyclohexylmethyl-N-methyl)amino]ethyl]-4-chromanol (isomers II; X=Y=H; $R_1$=CH$_3$; A=0; m=1; n=5)

The intermediate is obtained by using LAH to reduce the amide prepared in the previous stage, according to the procedure described in Example 2 - Stage 2.

Yld.=88.8%

TLC: Rf=0.75-0.90 (methylene chloride/methanol, 10% NH₄OH - 90:10 v/v)

Stage 3: 3-[2-[(N-cyclohexylmethyl-N-methyl)amino]ethyl]-4-chromanone (I.a; X=Y=H; $R_1$=CH$_3$; A=0; m=1; n=5)

Obtained by oxidation of the amino-alcohol obtained in the previous stage, according to the procedure described in Example 2 - Stage 3.

Yld.=65,8%

TLC: Rf=0.90 (methylene chloride/methanol, 10% NH₄OH - 95:5 v/v)

Hydrochloride

Yld=59% M.p.=204-205° C.

TLC: Rf=0.85 (methylene chloride/methanol, 10% NH₄OH - 95:5 v/v)

Analysis ($C_{19}H_{28}ClNO_2$) C, H, Cl, N, O

IR (KBr): 2900, 2850, 2600, 1680, 1600, 1480, 1290, 1120, 930, 750 cm$^{-1}$

NMR: 0.5-2.65 (m, 17H); 2.15 (s, 3H); 2.65-3.05 (m, 1H); 4.1-4.7 (m, 2H); 6.7-7.1 (m, 2H); 7.25-7.55 (m, 1H); 7.7-7.95 (m, 1H)

EXAMPLE 16

3-[2-[(N-Cyclohexylmethyl-N-Methyl)Amino]-Ethyl]-6-Fluoro-4-Chromanone Hydrochloride (Formula I.a; X=F; Y=H; $R_1$=CH$_3$; A=0; m=1; n=5)

Stage 1: N-cyclohexylmethyl-N-methyl-2-[(6-fluoro-4-chromanone)-3-yl]-acetamide (III; X=F; Y=H; $R_1$=CH$_3$; A=0; m=1; n=5)

This intermediate is prepared by condensing 2-(6-fluoro-4-chromanone)-acetic acid with N-cyclohexylmethyl-methylamine according to the procedure described in Example 15 - Stage 1 above. Yld.=95%

TLC: Rf=0.60 (ethyl acetate/hexane - 70:30 v/v)

Stage 2: 3-[2-[(N-cyclohexylmethyl-N-methyl)amino]ethyl]-6-fluoro-4-chromanol (isomers II; X=F; Y=H; $R_1$=CH$_3$; A=0; m=1; n=5)

Prepared by reduction using LAH, as described in Example 2 - Stage 2. Yld.=67%

TLC: Rf=0.70–0.80 (methylene chloride/methanol, 10% Na₄OH - 95:5 v/v)

Stage 3: 3-[2-[(N-cyclohexylmethyl-N-methyl)amino]ethyl]-6-fluoro-4-chromanone (I.a; X=F; Y=H; R₁=CH₃; A=O; m=1; n=5)

Prepared according to Example 2 - Stage 3. Yld.=64%

TLC: Rf=0.90 (methylene chloride/methanol, 10% NH₄OH - 95:5 v/v)

Hydrochloride

Yld.=80% M.p.=228°–230° C.

TLC: Rf=0.80–0.85 (methylene chloride/methanol, 10% NH₄OH - 95:5 v/v)

Analysis (C₁₉H₂₇ClFNO₂) C, H, Cl, F, N, O

IR (KBr): 2800, 2750, 2600, 1685, 1620, 1490, 1430, 1280, 820, 740 cm⁻¹

NMR: 0.4–2.6(m, 17 H); 2.15(s, 3H); 2.6–3.05 (m, 1H); 4.1–4.7(m, 2H); 6.8–7.3 (m, 2H); 7.4–7.65 (m, 1H);

EXAMPLE 17

2-[2-[(N-Allyl-N-Methyl)Amino]Ethyl]-1-Oxo-1,2,3,4-Tetrahydronaphthalene Hydrochloride (Formula I.a; X=Y=H; A=CH₂; R₁=CH₃; m=1; n=1)

Following the procedure described in Example 2 from 1-oxo-1,2,3,4-tetrahydro-2-naphthalene-acetic acid and N-allyl-methylamine, the following compounds are successively obtained in Stages 1–3.

Stage 1: N-allyl-N-methyl-2-[2-(1-oxo-1,2,3,4-tetrahydronaphthyl)]-acetamide (III; X=Y=H; A=CH₂; R₁=CH₃; m=1; n=1) Yld.=75%

TLC: Rf=0.70–0.80 (ethyl acetate)

Stage 2: 2-[2-[(N-allyl-N-methyl)amino]ethyl]-1-hydroxy1,2,,4-tetrahydronaphthalene (isomers II; X=Y=H; A=CH₂; R₁=CH₃; m=1; n=1) Yld.=83%

TLC: Rf=0.50–0.60-0.70 (methylene chloride/methanol, 10% NH₄OH - 95:5 v/v)

Stage 3: 2-[2-[(N-allyl-N-methyl)amino]ethyl]-1-oxo-1,2,3,4 tetrahydronaphthalene (I.a; X=Y=H; A=CH₂; R₁=CH₃; m=1; n=1) Yld. =74% (violet oil)

TLC: Rf=0.40–0.50 (methylene chloride/methanol, 10% NH₄OH - 95:5 v/v)

Hydrochloride

Yld.=57.9% M.p.=132–134° C.

TLC: Rf=0.40–0.60 (methylene chloride/methanol, 10% NH₄OH - 95:5 v/v)

Analysis (C₁₆H₂₂ClNO) C, H, Cl, N, O

IR (KBr): 2900, 2600, 2500, 1680, 1600, 1440, 1305, 1290, 1220, 1100, 740 cm⁻¹

NMR: 1.4–2.7(m, 7H); 2.25 (s, 3H); 2.85–3.01 (m, 4H); 5.0–5.3(m, 2H); 5.65–6.1(m, 1H); 7,1–7,55 (m, 3H); 7.90–8.1(m, 1H)

The compounds of the invention (I) and their salts showed their capacity for interaction with sigma receptors in biochemical and pharmacological screening tests carried out "in vitro" with the ligands (+)—[³H]-SKF10,047 and [³H]-DTG, which ligands detect the binding affinities of the compounds under study for sigma receptors. Tests of binding to phencyclidine and dopamine D₂ receptors were carried out to study the possible undesirable interactions of the compounds of the invention with these receptors. The ligands used are [³H]-TCP for phencyclidine and [³H]spiroperidol for dopamine.

Moreover, "in vivo" tests enabled the capacity of the compounds of the invention (I) to inhibit convulsions induced by electric shocks in rats, and also their capacity to inhibit gastroduodenal ulcers caused by administration of cysteamine, to be detected.

1) "In vitro" study

The binding experiments are carried out with the sigma ligands (+)—[³H]-SKF10,047 and [³H]-TCP according to the technique described by Largent B. L. et al. in J. Pharmacol. Exp. Ther. 238, 1986, p 739–748, the principle of which is to place in competition the respective affinities of the product under study and that of a radioactive characteristic ligand for sigma receptors.

Binding with the ligand [³H]-DTG is carried out according to the technique of Weber, E. M. et al., 1986, Proc. Natl. Acad. Sci., 83:8784–8788, and binding with the ligand [³H]spiroperidol is carried out according to the technique of Fields, J. Z., Reisine, R. D. and Yamamura, H. 1., Brain Res., 136,578 (1977).

The technique consists in incubating solutions of suitable concentrations of the test products with standard samples of membranes loaded with the labeled ligand, and then in determining the radioactivity of the solution after filtration.

The results are processed so as to calculate the IC₅₀ of the product under study, which represents the nanomolar concentration of solution capable of inhibiting 50% of the binding of the tritiated ligand to the sigma receptors of the membranes used. They are presented in Tables 1.A and 1.B below, in comparison with the results obtained with haloperidol chosen as reference compound.

The SKF 10,047 binding tests are performed with guinea pig or rat brain membranes, those with DTG and TCP are performed with rat brain membranes; the D₂ binding tests are performed with guinea pig brain membranes.

TABLE 1.A

| | IN VITRO BINDING TESTS | | | |
|---|---|---|---|---|
| PRODUCT TESTED | SKF10047 guinea pig IC₅₀ (nM) | DTG guinea pig IC₅₀ (nM) | PCP guinea pig IC₅₀ nM | D₂ rat IC₅₀ (nM) |
| EXAMPLE 2 | 12 | 52.00 | >10000 | >10000 |
| EXAMPLE 3 | 5.24 | n.d. | >10000 | 1172 |
| EXAMPLE 4 | 2.83 | 56.00 | >10000 | 1910 |
| Haloperidol | 8.95 | 22.67 | 1268 | 2 | n.d.: not done.

TABLE 1.B

| SIGMA BINDING RESULTS (SKF 10,047/rat brain membranes) | |
|---|---|
| PRODUCT TESTED | IC₅₀ (nM) |
| EXAMPLE 1 | 10.7 |
| EXAMPLE 2 | 19.4 |
| EXAMPLE 3 | 11.1 |
| EXAMPLE 4 | 10.6 |
| EXAMPLE 5 | 8.2 |
| EXAMPLE 6 | 8.0 |
| EXAMPLE 9 | 10.4 |
| EXAMPLE 10 | 5.7 |
| EXAMPLE 11 | 6.6 |
| EXAMPLE 12 | 30.5 |
| EXAMPLE 13 | 7.7 |
| EXAMPLE 14 | 13.7 |
| EXAMPLE 15 | 5.7 |
| EXAMPLE 16 | 6.2 |
| EXAMPLE 17 | 13.3 |

TABLE 1.B-continued

SIGMA BINDING RESULTS
(SKF 10,047/rat brain membranes)

| PRODUCT TESTED | IC$_{50}$ (nM) |
|---|---|
| Haloperidol | 24.6 |

The results show that the products of the invention (I), illustrated by the compounds of the above examples, have a manifest specificity of affinity for sigma receptors which is greater in intensity than that shown by haloperidol. Furthermore, and remarkably in comparison with this reference product, results from Table 1.A show that the compounds of the invention (I) have an affinity which may be regarded as zero for the PCP receptors, and likewise a zero or else negligible affinity for D$_2$ receptors, which is indicative of their therapeutic value.

2) "In vivo" study a) Convulsions in rats: electric shock

The psychotropic properties of the compounds (I) were determined by the protection against convulsions induced by electric shocks in rats.

The emission of an electric shock causes a convulsive state in the animal, characterized by the convulsive extension of front and rear legs.

In practice, the study is carried out on groups of 10 male Sprague Dawley rats weighing approximately 100 grams, to which the product under study is administered subcutaneously in aqueous solution on the basis of 0.5 ml per 100 grams of the animal's body weight.

An electric shock is then produced 30 minutes after the injection by means of a UGO BASILE ECT UNIT 7801 electric shock apparatus (APELEX): frequency 50 cps/sec, pulse width 0.6 ms, shock duration 1 sec, intensity 90 mA. Under these experimental conditions, the animals exhibit tonic convulsions which manifest themselves in an extension of the front and rear legs. Each animal then receives a score, which is equal to 1 for the presence of tonic convulsions and zero for the absence of tonic convulsions. In each group, the percentage of animals not exhibiting convulsions is calculated. The results are compared statistically between the control group and the treated group by the test of Fisher R. A. and Yates F. (Biometrika, 1948, 35–149) and the ED$_{50}$ (dose of the test compound giving rise to protection in 50% of the animals) is calculated by the method of Litchfield J. T. and Wilcoxon F. (J. Pharmacol. Exp. Therap., 1949, 96–99).

The results of the study are reported for the products of the invention in Table 2.

b) Cysteamine-induced ulcer

The activity of the compounds of the invention with respect to the gastrointestinal tract was shown in rats by their capacity to inhibit gastroduodenal ulcers caused by administration of cysteamine. (Robert and al., Digestion, 1974, 11, 199–211).

In practice, the study is carried out according to the method described by Selye, H. and Szabo, S., Nature, 1973, 244:458–459 on groups of male Sprague Dawley rats weighing 200 g on average, to which a solution of cysteamine hydrochloride is administered by subcutaneous injection on the basis of 400 mg/kg, the test products being administered to the animals orally or intraduodenally hour thirty minutes before the ulcerogenic agent. Eighteen hours later, the rats are sacrificed by elongation, and the stomach and duodenum are removed, rinsed with physiological solution and pinned onto a card. The presence of ulcers of the antropyloroduodenal region is looked for, and their area, expressed in mm$^2$, is evaluated by multiplying the two principal perpendicular axes of the lesion. Statistical analysis of the results is carried out using Student's test for the ulcerated areas in comparison with a control group. The results are presented in Table 2, and expressed as an ED$_{50}$ of ulceration scores, which are the effective doses of product in (mg/kg) for a 50% inhibition of the cysteamine-induced ulcers.

TABLE 2

| | IN VIVO TESTS | |
|---|---|---|
| PRODUCTS TESTED | Cysteamine ulcer ED$_{50}$ mg/kg | Electric shocks ED$_{50}$ mg/kg |
| EXAMPLE 2 | n.d. | 0.1 |
| EXAMPLE 3 | 8.6 (po) 5.7 (ip) | 0.9 |
| EXAMPLE 4 | 15.6 (po) | 1.0 |
| EXAMPLE 10 | n.d. | 1.6 |
| EXAMPLE 12 | 11.6 (ip) | 1.7 |
| EXAMPLE 14 | n.d. | 3.5 |

(po) = oral route
(ip) = intraperitoneal route
n.d. = not done

The acute toxicity of the products of the invention was investigated after oral administration in rats, which enabled an approximate value of their LD$_{50}$, which is the lethal dose causing death in 50% of the animals under the conditions of the experiment, to be determined. At doses close to one hundred times as high as their physiologically active dose, this toxicity was considered to be negligible.

These pharmacological properties, as described, combined with the low toxicity of the compounds of the invention, make it possible to envisage their usefulness in the form of medicinal products for preventive and curative treatment of conditions giving rise to certain mental disorders, in particular psychotic states such as depressive states, memory and behavioral disorders, stress and anxiety, as well as in the case of dysfunctions of the gastrointestinal tract such as, for example, various ulcers including those linked to stress.

The dosages are commonly between 1 and 1000 mg, and more especially 5 and 500 mg, of product, depending on the nature and the severity of the condition to be treated. These daily therapeutic dosages may be divided into several doses. Generally speaking, a daily dosage of 5 mg to 500 mg of product divided into two to four doses yields a satisfactory therapeutic result.

The administration of the products of the invention to the patients to be treated is carried out in the form of medicinal products whose nature is suited to the condition to be treated.

Depending on the case, the medicinal preparations will be, as non-limiting examples, tablets, drages, capsules, powders, solutions, suspensions, gels or suppositories. These various pharmaceutical dosage forms are prepared from the products in base form or in the form of their salts, and according to methods commonly employed in pharmaceutical practice.

Generally, in the medicinal forms of a "solid" nature, the active principle represents from 2 to 50% by weight of the total of the finished dosage form, while the excipients represent from 98 to 50%. For the "liquid" dosage forms, or those which may be regarded as such, the quantity of active principle is between 0.1 and 10% by weight of the finished dosage form, while the excipients can represent from 99.9 to 90% by weight of this dosage form.

As an illustration, the formula and preparation of tablets and of isotonic solution with the compound of Example 2 are described.

| Tablets | |
|---|---|
| Formula: | |
| active principle (compound of Example 2) | 10.0 to 50.0 mg |
| polyvinylpyrrolidone | 20.0 mg |
| carboxymethyl starch | 8.0 mg |
| magnesium stearate | 2.0 mg |
| colloidal silica | 0.4 mg |
| lactose q.s. | 200.0 mg |

Preparation

The active principle in aqueous-alcoholic solution is mixed with the lactose and then granulated with the polyvinylpyrrolidone, which is also in solution. The particles are dried and sieved through a screen of aperture 1 mm. The carboxymethyl starch is mixed with the colloidal silica and then added to the granules. An intimate mixture is then made with the magnesium stearate, and the preparation is then tabletted on the basis of 200.0 mg per tablet.

| Injectable isotonic solution | |
|---|---|
| Formula: | |
| active substance (I), hydrochloride of Example 2 | 10.0 mg |
| sodium chloride | 9.0 mg |
| distilled water q.s. | 1.0 ml |

Preparation

The isotonic solution is distributed in ampoules of suitable volume, which are, after sealing, sterilized by customary thermal means, or else the solution is sterilized by filtration and distributed in ampoules which are then sealed, all of these operations being carried out under a sterile atmosphere.

We claim:

1. New cycloalkylalkylamines which are sigma-receptor ligands of general formula (I)

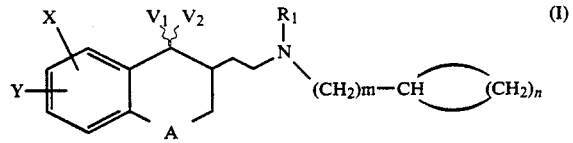

in which:
R$_1$ is H or lower alkyl;
X and Y, which may be identical or different, are H, OH, lower alkyl, lower alkoxy, halogen or nitrile;
V$_1$ and V$_2$ together form a double bond attached to an oxygen atom or else to a hydroxyimino radical N—OH, or else are linked as an ethylenedioxy chain —O—CH$_2$—CH$_2$—O—;
A represents a valency bond, an oxygen atom, a methylene group or alternatively an ethylene group;
m is equal to 1 or 2;
n has the value of an integer from 2 to 5; and their addition salts with pharmaceutically acceptable acids.

2. Compounds according to claim 1, characterized in that V$_1$ and V$_2$ together form a double bond attached to an oxygen atom.

3. Compounds according to claim 1, characterized in that A represents a methylene group.

4. Compounds according to claim 1, characterized in that R$_1$ is CH$_3$.

5. Compounds according to claim 1, characterized in that n=2 or 3.

6. Compounds according to claim 2, characterized in that X and Y are each H, m is 1 or 2 and n is 2 or 3.

7. Compounds according to claim 6, characterized in that A represents a valency bond, n is 2, and R$_1$ is CH$_3$.

8. Compounds according to claim 6, characterized in that A represents a methylene group and R$_1$ is CH$_3$ or C$_3$H$_7$.

9. Compounds according to claim 6, characterized in that R$_1$ is CH$_3$ and A represents an ethylene group or O.

10. Compounds according to claim 6, characterized in that X and Y are each H, A represents a methylene group, R$_1$ is CH$_3$, m is 1 and n is 2.

11. Compounds according to claim 2, characterized in that Y is H, R$_1$ is CH$_3$, m is 1 and n is 5.

12. Compounds according to claim 11, characterized in that X is H or 6—O—CH$_3$ and A represents a methylene group.

13. Compounds according to claim 11, characterized in that X is H and A represents an ethylene group or O.

14. Compounds according to claim 11, characterized in that X is F and A represents O.

15. Compounds according to claim 1, specifically as 2-[2-[(N-cyclopropylmethyl-N-methyl)amino]-ethyl]-1-[spiro(cyclodioxyethyl)]-1,2,3,4-tetrahydronaphthalene or 2-[2-[(N-cyclobutylmethyl-N-methyl)amino]-ethyl]-1-hydroxyimino-1,2,3,4-tetrahydronaphthalene.

16. Cycloalkylalkylamines of formula (I) which are:
2-[2-[(N-cyclobutylmethyl-N-methyl)amino]ethyl]-1-oxo-1,2,3,4-tetrahydronaphthalene and its hydrochloride, and
2-[2-[(N-cyclopropylethyl-N-methyl)amino]ethyl]-1-oxo-1,2,3,4,-tetrahydronaphthalene and its hydrochloride.

17. Medicinal product to combat mainly disorders induced by a derangement of the physiological mechanisms controlled by sigma receptors, in mammals or in man, characterized in that it comprises a cycloalkylalkylamine (I)

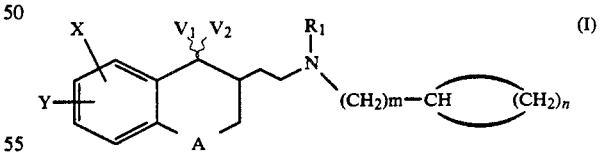

in which:
R$_1$ is H or lower alkyl;
X and Y, which may be identical or different, are H, OH, lower alkyl, lower alkoxy, halogen or nitrile;
V$_1$ and V$_2$ together form a double bond attached to an oxygen atom or else to a hydroxyimino radical N—OH, or else are linked as an ethylenedioxy chain —O—CH$_2$—CH$_2$—O—;
A represents a valency bond, an oxygen atom, a methylene group or alternatively an ethylene group;
m is equal to 1 or 2;

n has the value of an integer from 2 to 5;

and their addition salts with pharmaceutically acceptable acids, with a therapeutically acceptable carrier.

18. Intermediate of formula (II)

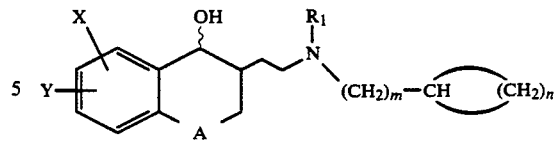

in which
R$_1$ is H or lower alkyl;
X and Y, which may be identical or different, are H, OH, lower alkyl, lower alkoxy, halogen or nitrile;
A represents a valency bond, an oxygen atom, a methylene group or alternatively an ethylene group;
m is equal to 0, 1 or 2;
n has the value of an integer from 1 to 5.

* * * * *